(12) United States Patent
Pelerin

(10) Patent No.: US 7,607,438 B2
(45) Date of Patent: Oct. 27, 2009

(54) MOUTH GUARD

(76) Inventor: Joseph J. Pelerin, 4498 Klais, Clarkston, MI (US) 48048

(*) Notice: Subject to any disclaimer, the term of this patent is extended or adjusted under 35 U.S.C. 154(b) by 82 days.

(21) Appl. No.: 11/624,301

(22) Filed: Jan. 18, 2007

(65) Prior Publication Data

US 2007/0181137 A1    Aug. 9, 2007

Related U.S. Application Data

(60) Provisional application No. 60/825,276, filed on Sep. 12, 2006, provisional application No. 60/761,890, filed on Jan. 25, 2006.

(51) Int. Cl.
*A61C 5/14* (2006.01)
*A61C 3/00* (2006.01)
*A61F 5/37* (2006.01)
*A61B 1/32* (2006.01)

(52) U.S. Cl. .............. 128/859; 128/860; 128/861; 128/862; 128/846; 433/6; 433/7; 600/240

(58) Field of Classification Search ........... 128/858, 128/862, 859, 860, 861, 846, 857; 433/6, 433/7, 18, 19, 24; 602/902; 600/240
See application file for complete search history.

(56) References Cited

U.S. PATENT DOCUMENTS

| 3,236,235 | A | * | 2/1966 | Jacobs ................... 128/862 |
| 5,033,480 | A | * | 7/1991 | Wiley et al. ............ 128/861 |
| 5,085,584 | A |   | 2/1992 | Boyd |
| 5,513,656 | A | * | 5/1996 | Boyd, Sr. ............... 128/859 |
| 5,566,684 | A |   | 10/1996 | Wagner |
| 5,795,150 | A |   | 8/1998 | Boyd |
| 5,865,619 | A | * | 2/1999 | Cross et al. ............ 433/6 |
| 6,626,180 | B1 |  | 9/2003 | Kittelsen et al. |
| 6,666,212 | B2 | * | 12/2003 | Boyd, Sr. ............... 128/859 |
| 7,234,467 | B2 | * | 6/2007 | Ball ....................... 128/848 |
| 2004/0144393 | A1 |  | 7/2004 | Conklin |
| 2004/0241606 | A1 | * | 12/2004 | Diesso ................... 433/37 |

FOREIGN PATENT DOCUMENTS

| JP | 3-244480 | 10/1991 |
| JP | 10-295706 | 11/1998 |
| JP | 11-42311 | 2/1999 |

OTHER PUBLICATIONS

"The Doctor's Night Guard—Dental Protector for Night Time Teeth Grinding", 2004 Dental Concepts, Paramus, Ny 07652.
"Bite Soft Anterior Splint", Trident Dental Laboratories, Advertisement, ADA News, Dec. 11, 2006.

* cited by examiner

*Primary Examiner*—Patricia M Bianco
*Assistant Examiner*—Ophelia Hawthorne
(74) *Attorney, Agent, or Firm*—Gifford, Krass, Sprinkle, Anderson & Citkowski, P.C.

(57) ABSTRACT

A mouth guard having a tray with a trough dimensioned to receive at least the front two incisors. Impression material is disposed within the trough for creating a dental impression of the wearer's teeth. The tray further includes a stiffening element which concentrates the force transmission through the tray created by occlusion to an area between the upper and lower front incisors.

14 Claims, 2 Drawing Sheets

MOUTH GUARD

CROSS-REFERENCE TO RELATED APPLICATIONS

This application claims priority of U.S. Provisional Patent Applications Ser. No. 60/761,890 filed Jan. 25, 2006 and Ser. No. 60/825,276 filed Sep. 12, 2006, which are incorporated herein by reference.

BACKGROUND OF THE INVENTION

I. Field of the Invention

The present invention relates generally to a mouth guard to minimize teeth grinding during sleep and reduce TMJ and other jaw-related problems.

II. Description of Material Art

Many persons have the tendency of grinding their teeth while sleeping. Such grinding of the teeth is involuntary and disadvantageously results in undesirable wear of the teeth, TMJ and other jaw-related problems.

In order to minimize the damage created by grinding of the teeth, there have been a number of previously known mouth guards which are positioned within the mouth between the teeth on the upper and lower jaws. These previously known mouth guards separate the upper and lower jaws from each other during sleep and thus prevent the teeth from grinding against each other involuntarily during sleep.

The previously known mouth guards, however, have not proven entirely satisfactory in operation. Although the previously known mouth guards effectively eliminate teeth grinding by separating the upper and lower teeth during sleep, they do not eliminate or even significantly reduce involuntary occlusion of the teeth during sleep. Consequently, while these previously known mouth guards effectively prevent erosion of the teeth caused by grinding during sleep, such guards provide little, if any, relief from temporomandibular joint disease (TMJ) and other jaw-related problems associated with teeth grinding.

SUMMARY OF THE PRESENT INVENTION

The present invention provides a mouth guard which overcomes the above-mentioned disadvantages of the previously known mouth guards.

In brief, the mouth guard of the present invention comprises a tray having a trough dimensioned to receive at least the front two upper or lower incisors. The tray is preferably constructed of a thin flexible plastic material such as polyethylene.

A dental impression material is disposed within the trough. Preferably, the dental impression material is polycapralactone based with an ethylene co-vinyl acetate additive which becomes pliable at an elevated temperature of, e.g., 135° F. or higher. The impression material, however, sets and retains its shape at a human body temperature, e.g. about 100° F.

In order to custom fit the mouth guard to an individual wearer, the tray containing the impression material is first heated to approximately 135° F. in any conventional fashion, such as immersing the tray in hot water. Once the impression material becomes pliable, the tray is positioned within the wearer's mouth so that the tray extends over at least the front two upper or lower incisors. The wearer then occludes into the pliable impression material and the impression material is allowed to cool and set. Thereafter, the impression material frictionally retains the tray in position in the mouth during use.

The tray further includes means for concentrating the force transmission through the tray caused by occlusion to the area between the upper and lower front incisors. In one form of the invention, a stiffening element is positioned within the tray so that the stiffening element is aligned with the front two incisors of the wearer. The stiffening element is less flexible or harder than both the tray and the impression material. Consequently, with the mouth guard positioned in the wearer's mouth, upon occlusion the force caused by the occlusion is concentrated by the stiffening element to the front incisors whereas the rest of the tray maintains its flexibility.

In yet another embodiment of the invention, the means for concentrating the force transmission through the tray caused by occlusion to the front incisors comprises a thickened area of the tray which is aligned with the front incisors. Like the stiffening element, a thickened portion of the tray is less flexible and thus harder than the remainder of the tray thereby concentrating the force transmission caused by occlusion to the front incisors.

The concentration of the force transmission caused by occlusion to the front incisors can result in an involuntary reflex to open the mouth. Consequently, during sleep, an involuntary occlusion concentrates that force of occlusion to the front incisors of the wearer thus helping to stimulate an immediate reflective opening of the mouth. This, in turn, not only prevents teeth grinding, but also may reduce TMJ and other jaw-related problems caused by occlusion or clenching of the teeth during sleep.

BRIEF DESCRIPTION OF THE DRAWING

The present invention will be more fully understood upon reference to the following detailed description, when read in conjunction with the accompanying drawing, wherein lice reference characters refer to like parts throughout the several views, and in which.

DETAILED DESCRIPTION OF PREFERRED EMBODIMENTS OF THE PRESENT INVENTION

With reference first to FIGS. 1-4, a first preferred embodiment of a mouth guard 10 according to the present invention is shown. The mouth guard 10 includes a tray 12 constructed of a thin plastic material, such as polyethylene. The tray 12, furthermore, defines an arcuate trough 14 dimensioned to receive at least the front upper or lower incisors. However, as illustrated in FIGS. 1-4, the tray 12 extends around a portion of the mouth encompassing not only the front incisors but also the front canine teeth.

Figure 6:
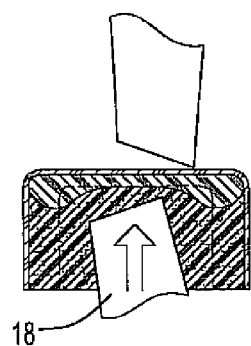
FIG. 6 is a view similar to FIG. 5 and illustrating a further step in customizing the mouth guard of the present invention.
Figure 5:
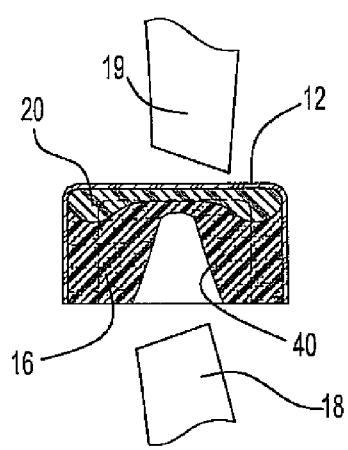
FIG. 5 is a view taken substantially along line 5-5 and illustrating the customization of the mouth guard.

With reference now particularly to FIGS. 5 and 6, a thermoplastic dental impression material 16 is disposed within the tray 12. The dental impression material 16 is preferably about 75% by weight polycapralactone and about 25% by weight ethylene co-vinyl acetate and, as such, becomes pliant at an elevated temperature, e.g. about 135° F. or higher. However, at body temperature, the impression material 16 sets and retains its shape.

Any other impression material, such as polyvinyl silicone, may alternatively be used, In order to create the dental impression in the impression material 16, the tray 12 with the impression material 16 is first heated until the impression material 16 becomes pliant. This may be easily accomplished by submersing the tray 12 with the impression material 16 in hot water until the impression material 16 becomes pliant. Furthermore, the compression material 16 adheres to the tray 12 either through natural adhesion between the impression material 16 and tray 12 or by mechanical interlock between the impression material 16 and tray 12, or both.

In order to facilitate immersion of the tray 12 and impression material 16, a string 60 (FIG. 1) is optionally embedded in the impression material 16 or tray 12. This string 60 may be removed when it is no longer required.

Once the dental impression material 16 is pliant, the tray 12, which retains its shape upon heating to about 135° F., is positioned in the mouth of the wearer as shown in FIG. 5. Upon occlusion of the teeth 18 and 19, as shown in FIG. 6, the dental impression material 16 molds around the teeth 18 of the wearer. Upon cooling, the dental impression material 16 retains its shape and thus the dental impression of the wearer.

Figure 4:
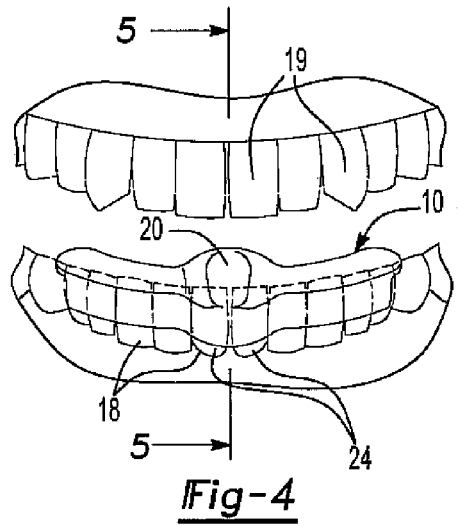
FIG. 4 is a front view illustrating an embodiment of the invention positioned within the mouth of a wearer.

As illustrated in FIG. 4, the tray 10 is illustrated as positioned over the lower teeth 18 of the wearer. However, this is by way of example only and the tray 10 may alternately be positioned over the upper teeth of the wearer.

Figure 1:
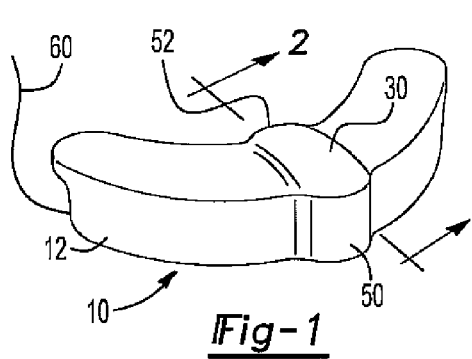
FIG. 1 is an elevational view illustrating an embodiment of the present invention.
Figure 2:
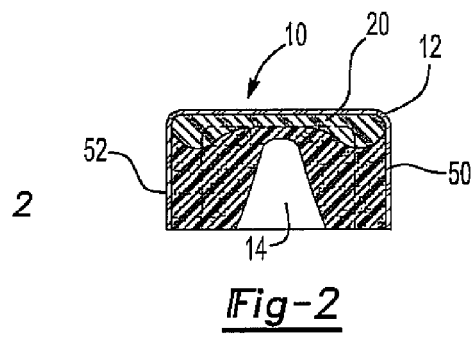
FIG. 2 is a view taken substantially along line 2-2 in FIG. 1.

As shown in FIG. 1, the tray also optionally includes an anteriorly projecting ledge 50 and/or posteriorly projecting ledge 52. These ledges 50 and 52 provide an occlusal surface and prevent the lower incisors from becoming entrapped behind the tray 12 if the tray 12 is positioned on the upper teeth, or the upper incisors from becoming entrapped in front of the tray 12 upon occlusion. The ledges help maintain contact of upper and lower teeth with different jaw structure variations.

Figure 3:
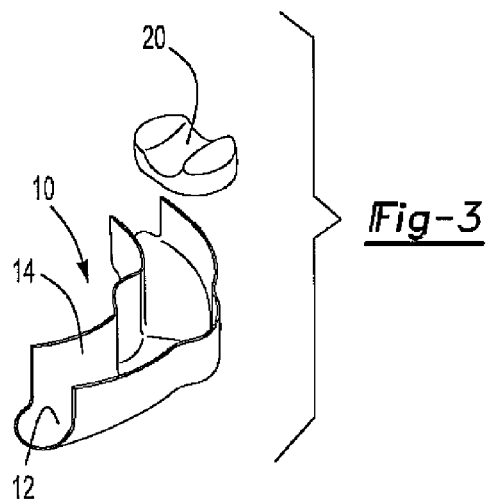
FIG. 3 is an exploded elevational view illustrating one embodiment of the present invention.
Figure 7:
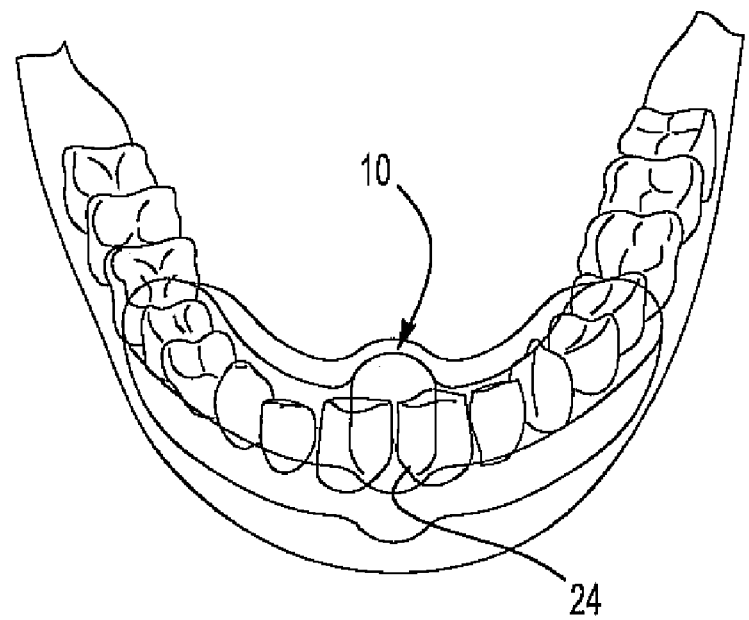
FIG. 7 is an elevational view of the mouth guard of the present invention positioned within the mouth.

With reference now particularly to FIGS. 3 and 7, the mouth guard 10 of the present invention includes means for concentrating the force transmission through the tray created by occlusion to the area between the upper and lower front incisors. As illustrated in FIGS. 3 and 4, in one embodiment of the invention, a stiffening element 20 is positioned within the tray 12 so that the stiffening element 20 is aligned with and overlies the front incisors of the wearer. The stiffening element 20 may comprise, for example, a hard plastic material, i.e. harder than the impression material 16 and rear portions of the tray 12, and may be attached to the tray 12 in any conventional way. For example, the stiffening element 20 may be simply embedded within the impression material 16 such that the impression material 16 secures the stiffening element 20 to the tray 12. Alternatively, the stiffening element 20 may be bonded to the tray 12 or embedded within the tray 12.

In use, the stiffening element 20 concentrates the force transmission through the tray caused by occlusion so that the force of occlusion is transmitted almost entirely to the front upper and lower two incisors. This, in turn, causes a reflective opening of the mouth immediately in response to such an occlusion. This, in turn, effectively prevents teeth grinding in most cases and reduces or eliminates TMJ and other jaw-related problems which are otherwise caused by clenching of the teeth during sleep.

Figure 8:
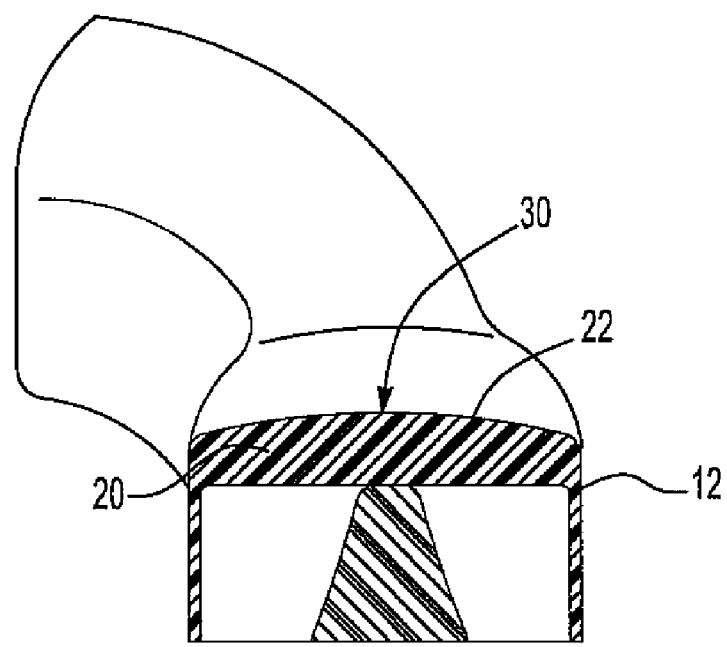
FIG. 8 is a partial sectional view illustrating a second preferred embodiment of the present invention.

With reference now to FIGS. 7 and 8, although the stiffening element 20 may comprise a separate component which is positioned within the tray 12. In the alternative, the stiffening element 20 comprises a thickened portion 22 in the tray 12 aligned with the front incisors 24 of the wearer's teeth. The thickened portion 22 of the tray 12 which forms the stiffening element 20 is less flexible or harder than the remainder of the tray 12 and serves to concentrate the force transmission through the tray created by occlusion to the area between the upper and lower front incisors of the wearer's mouth. The thickened portion 22 may also form a hump 30 as shown in FIGS. 1 and 8 which protrudes outwardly from the tray. This hump 30 ensures force transmission to the front incisors upon occlusion.

From the foregoing, it can be seen that the mouth guard of the present invention achieves many advantages over the previously known mouth guards. In particular, the impression material 16, after being custom fit to the wearer's mouth, frictionally and comfortably retains the mouth guard in position following insertion. Furthermore, since the impression material 16 is a thermoplastic material, the dental impression may be redone at any time by merely heating the impression material 16 up to its pliant temperature and then forming a new dental impression.

Since the mouth guard of the present invention prevents or minimizes clenching of the teeth during sleep, TMJ and other jaw-related problems are greatly reduced and/or eliminated.

Having described my invention, however, many modifications thereto will become apparent to those skilled in the art to which it pertains without deviation from the spirit of the invention as defined by the scope of the appended claims.

I claim

1. A mouth guard comprising:
   a tray having a trough and dimensioned to receive at least two front mandibular incisors,
   impression material disposed in said trough,
   a stiffening element in said tray which concentrates the force transmission through said tray created by occlusion to the area between upper and lower front incisors, said stiffening element being aligned only with the two front incisors and constructed of a material harder than said impression material and harder than the portions of said tray extending rearwardly from the front incisors.

2. The invention as defined in claim 1 wherein said impression material comprises a thermoplastic material which is pliable at an elevated temperature above 135° Fahrenheit and sets at a human body temperature.

3. The invention as defined in claim 2 wherein said impression material comprises polycapralactone.

4. The invention as defined in claim 2 wherein said impression material comprises polycapralactone with an ethylene co-vinyl acetate additive.

5. The invention as defined in claim 1 wherein said stiffening element comprises a thickened portion of said tray.

6. The invention as defined in claim 5 wherein said thickened portion is about 4 millimeters thick.

7. The invention as defined in claim 5 wherein said thickened material comprises a hump which protrudes outwardly from said tray.

8. The invention as defined in claim 1 wherein said tray comprises a flexible plastic material.

9. The invention as defined in claim 8 wherein said tray comprises polyethylene.

10. The invention as defined in claim 1 and comprising a ledge attached to and extending laterally outwardly from said tray.

11. The invention as defined in claim 10 wherein said ledge forms a tooth stop upon occlusion.

12. The invention as defined in claim 1 wherein said impression material comprises polyvinyl silicone.

13. The invention as defined in claim 1 and comprising a string embedded in said impression material so that a portion of said swing extends outwardly from said impression material.

14. The invention as defined in claim 1 and comprising a string attached to said tray so that a portion of said string extends outwardly from said tray.

* * * * *